United States Patent [19]
Butterbrodt

[11] Patent Number: 5,125,423
[45] Date of Patent: Jun. 30, 1992

[54] APPLICATOR FOR TREATING THE SKIN

[75] Inventor: Gerhard Butterbrodt, Berlin, Fed. Rep. of Germany

[73] Assignee: Schering, Aktiengesellschaft, Berlin & Bergkamen, Fed. Rep. of Germany

[21] Appl. No.: 601,755

[22] PCT Filed: Apr. 20, 1989

[86] PCT No.: PCT/DE89/00259

§ 371 Date: Oct. 29, 1990

§ 102(e) Date: Oct. 29, 1990

[87] PCT Pub. No.: WO89/10075

PCT Pub. Date: Nov. 2, 1989

[30] Foreign Application Priority Data

Apr. 29, 1988 [DE] Fed. Rep. of Germany ....... 8805927

[51] Int. Cl.⁵ .............................................. A45D 24/22
[52] U.S. Cl. .................................... 132/112; 132/114; 401/28; 401/186; 401/191
[58] Field of Search ................ 401/191, 186, 28, 219; 132/112–116

[56] References Cited

U.S. PATENT DOCUMENTS

| | | | |
|---|---|---|---|
| 1,067,930 | 7/1913 | Lewinski | 132/112 X |
| 1,113,843 | 10/1914 | Smith | 132/114 |
| 1,429,635 | 9/1922 | Ross | 132/114 X |
| 1,615,581 | 1/1927 | Harris | 401/28 X |
| 1,686,981 | 10/1928 | Olson | 132/114 |
| 2,379,330 | 6/1945 | Wilensky | 401/28 |
| 2,624,348 | 1/1953 | Matson | 132/114 |
| 2,956,570 | 10/1960 | Stanford | 132/116 |
| 3,101,086 | 8/1963 | Di Vito | 132/114 |
| 3,456,658 | 7/1969 | Long, Jr. | 132/116 |
| 4,049,354 | 9/1977 | O'Rourke | 401/186 X |
| 4,543,913 | 10/1985 | Wilkeson | 132/114 X |

FOREIGN PATENT DOCUMENTS

| | | | |
|---|---|---|---|
| 1252647 | 12/1960 | France | 132/114 |
| 2078175 | 1/1982 | United Kingdom | 401/219 |

Primary Examiner—Steven A. Bratlie
Attorney, Agent, or Firm—Millen, White & Zelano

[57] ABSTRACT

An applicator for treating the skin dispenses a predetermined dose of treatment agent. The applicator comprises a cylindrical portion, the front face of which is open, and a closure piece for the open front face. Solid and hollow pins extend axially from a front wall of the cylindrical portion. The hollow pins communicate with the cylinder cavity. The closure piece and the cylindrical portion are designed so that the closure piece delimits a given volume in the cylindrical portion. The closure piece has a central filling opening with a non-return or one-way valve disposed therein.

7 Claims, 4 Drawing Sheets

APPLICATOR FOR TREATING THE SKIN

BACKGROUND OF THE INVENTION

The invention relates to an applicator for treating the skin and more particularly to an applicator which disperses fluid through tubular projections.

An applicator is known from DE 31 22 516 A1 in which a closure member receives a plunger with which an agent for treating the scalp is pushed out of the applicator. When the applicator is open, the cylinder interior must be filled by pouring or pushing in the treatment agent. An exact dosage of the agent is not possible.

German utility model specification 18 03 642 describes a device for applying substances to the scalp. This device can be screwed onto a supply bottle. With this applicator exact dosage of the treatment agent is not possible.

An object of the invention is to make an applicator of the above-described type which can be used as a hand-operated device and with which a precisely dosed amount of a treatment agent is dispensed. This requirement is essential especially in the application of medicines, which is to be done at certain times in precisely predetermined doses.

The closure piece delimits within the cylinder, particularly advantageously, a cylindrical interior within with a fixed, predetermined volume and includes central filling opening in which a nonreturn device is monitored. It is possible to fill the cylindrical interior with a precisely dosed amount of treatment agent using a supply bottle or a supply tube. After filling, the nonreturn device prevents the treatment agent from leaking back into the supply bottle or tube.

The design, according to the invention, of the applicator makes it possible to attach the applicator to a supply container. Further, it is advantageously possible, after filling the applicator, to separate it from the supply container and to use it as a hand-operated device.

Advantageously, the volume of the cylindrical interior delimited by the closure piece is in the range of 0.1 to 5 ml, in particular in the range of 0.25 to 2.5 ml.

In an advantageous embodiment, the nonreturn device is made as a nonreturn device connecting piece. This nonreturn device connecting piece extends from the central filling opening into the cylinder interior and, after a filling and a twisting of the applicator, prevents leakage.

In another advantageous embodiment of the applicator, in the filling opening there is provided a valve seat surrounded by a cage in which a free-floating valve body is placed. The valve is especially advantageously configured as a ball valve.

Because cosmetics or pharmaceuticals provided for skin treatment are often supplied in small bottles, especially plastic bottles, that exhibit a pump or dispenser mechanism, the applicator can advantageously be made so that it can be used together with such dispenser or supply vessels. For this purpose, at least one positively locking seat for a supply vessel or a supply bottle is formed on the closure piece.

Advantageously, the closure piece is made to be insertable into the open front face of the cylinder. The closure piece can, for example, be solidly connected to the cylinder by impact or by ultrasonic welding. In another embodiment, the closure piece has an outer thread and the cylinder has an inner thread which mesh to connect the pieces together.

A knurl is provided on the periphery of the cylinder for easier handling.

A protective cap that can be placed on the cylinder is provided to protect the applicator.

The applicator exhibits a cylinder open on the front face and able to be closed by a closure piece. In this way, a supply chamber is formed inside the cylinder. Axially extending solid and hollow pins are made on the front wall of the cylinder. The hollow pins lead into the cylinder interior and exhibit an opening on the tip. When using this applicator, medicines or cosmetics contained in the cylinder can be dispensed through the hollow pins to the skin to be treated and can be massaged into the skin by a suitable massage movement of the solid pins placed on the cylinder. Doses for certain medicines or cosmetics can be adjusted by dimensioning the cross sections of the hollow pins.

Advantageously, the solid and hollow pins are cone-shaped.

To increase stability, the diameters of the solid pins are made smaller in their radial planes than the diameters of the hollow pins. To achieve a good massage effect, the tips of the solid pins are rounded.

Advantageously, the tips of the hollow pins are rounded and the opening is made as a slit in the shape of a cross. An especially favorable treatment effect is achieved by placing the solid and hollow pins each in alternation on the front wall in concentric circles. In doing so, the circle of largest diameter (the edge circle) is occupied by solid pins and a hollow pin is placed at the center of the front wall.

To adapt to curvatures of the skin surface, especially in the region of the scalp, the tips of the solid and hollow pins lie on an enveloping conical surface.

BRIEF DESCRIPTION OF THE DRAWINGS

Embodiments of the invention are to be explained in the following description with reference to the FIGURES of the drawing.

There are shown in.

DETAILED DESCRIPTION

Figure 1:
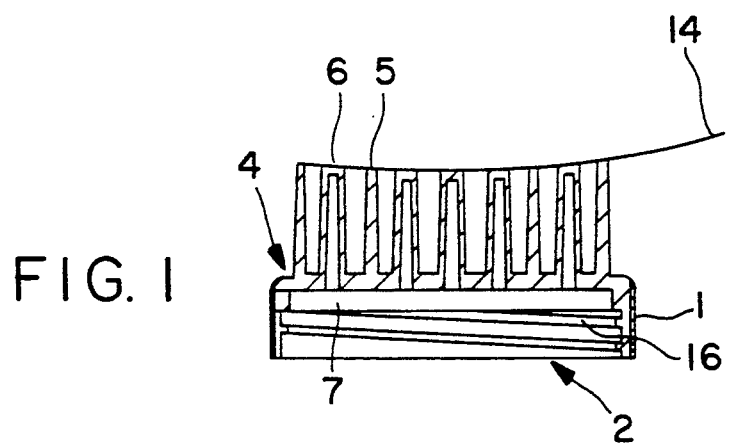
FIG. 1, a sectional view of the cylindrical member of the applicator.

As FIG. 1 shows, a cylinder 1 open on front face 2 is provided. Solid pins 5 and hollow pins 6 extend axially from front wall 4 of the cylinder.

Open front face 2 of the cylinder can be closed by a closure piece 3, embodiments of which are represented in FIGS. 3A and 3B and 4A-4C. The closure piece 3 can be connected to cylinder 1 solidly and undetachably. In the embodiments represented, cylinder 1 exhibits an inner thread 16 and the embodiments of closure piece 3 exhibit an outer thread 15, so that both these parts can be screwed to one another. A hollow space 7 represented in FIGS. 1 and 5 is defined between these parts.

Figure 5A:
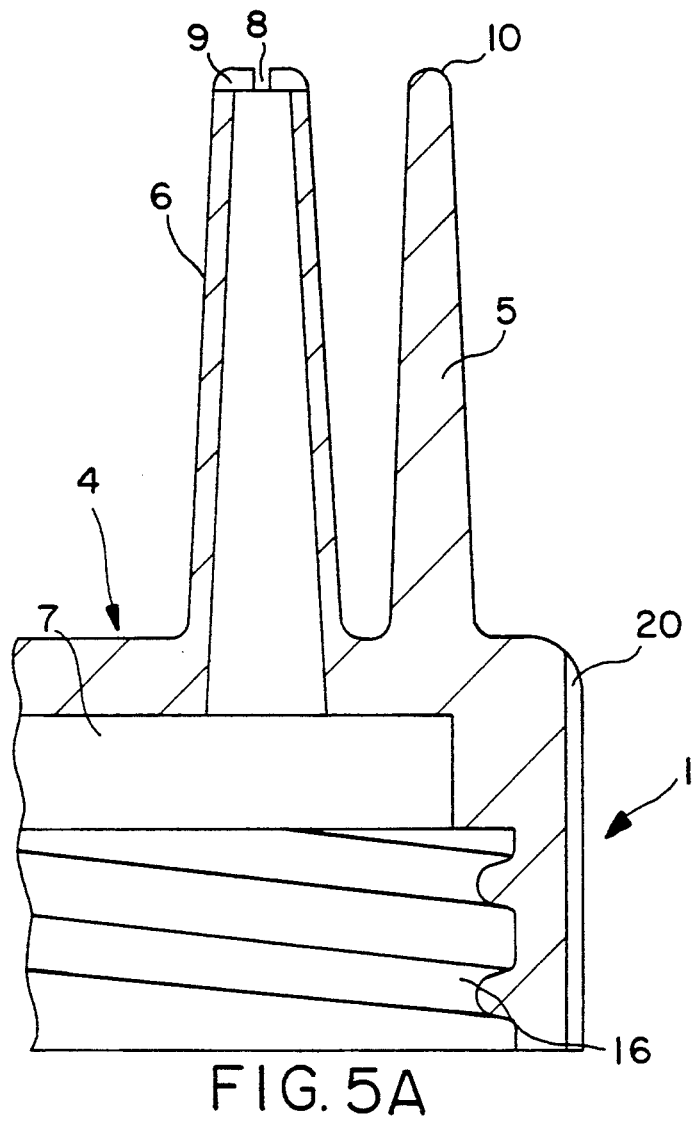
Figure 5B:
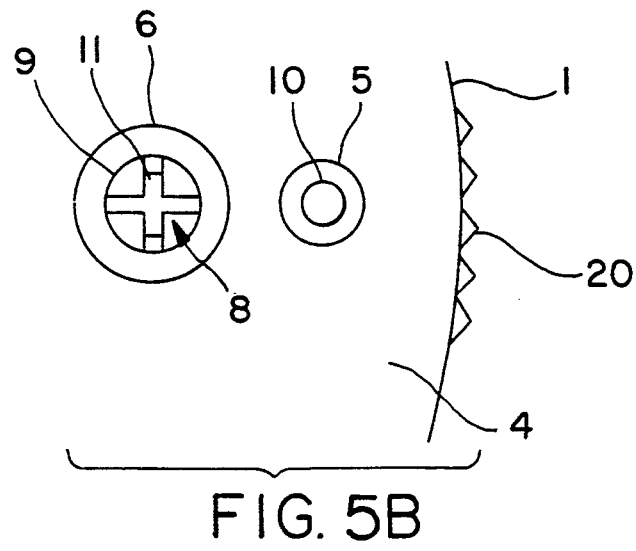

As can be seen especially in FIG. 5, the hollow pins 6 lead into a supply or hollow space 7 and exhibit an opening 8 on their tips 9. Cosmetics or pharmaceuticals located in the hollow space or supply space 7 can exit through hollow pins 6, when the applicator is used, onto the skin sections to be treated and are massaged into the skin by a massage movement by solid pins 5.

Figure 2:
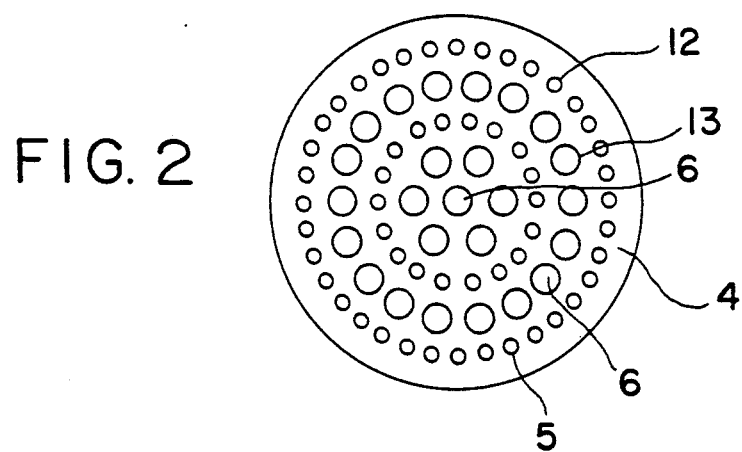
FIG. 2, a top view of the cylindrical member represented in FIG. 1.

As FIG. 2 shows, solid pins 5 and hollow pins 6 are arranged in alternation in concentric circles. Outer circle 12 is occupied by solid pins 5, and immediately following, circle 13 is occupied by hollow pins 6. A hollow pin 6 is located in the center.

As FIG. 1 shows, the solid and hollow pins 5 and 6 have differing lengths. The design is such that the tips of all solid and hollow pins lie on an enveloping conical surface, which is indicated diagrammatically in FIG. 1 at 14.

Figure 3A:
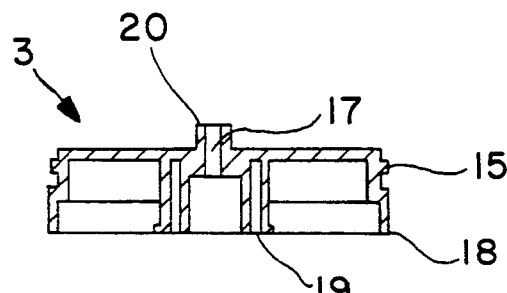
FIGS. 3A and 3B, a sectional view and a top view of an embodiment of the closure piece for the cylindrical member, FIGS. 4A-4C, representations of a closure piece with nonreturn valve, FIG. 5, an enlarged representation of structural details of the cylindrical member, and FIG. 6, a sectional view of a protective cap.
Figure 3B:
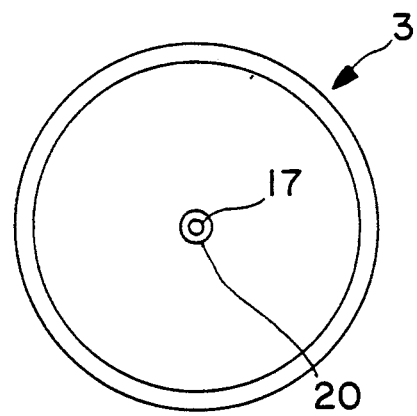

Closure piece 3 represented in FIG. 3A and 3B exhibits a filling opening 17 in the center. Further, seat mountings 18 and 19 are provided on closure piece 3. As FIGS. 3A and 3B show, filling opening 17 is surrounded by a nonreturn device sleeve 20. The sleeve 20 prevents the liquid dispensed into cylinder interior 7 during use of the applicator from again leaking through filling opening 17.

Figure 4A:
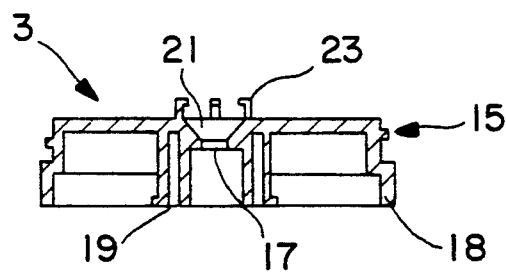
Figure 4B:
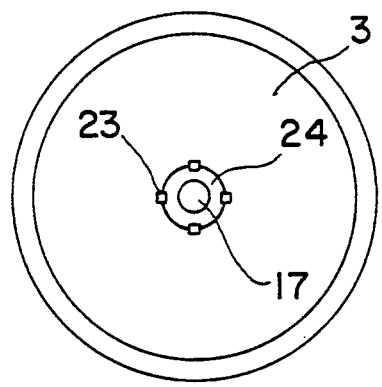
Figure 4C:
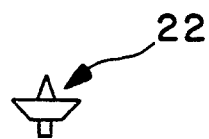

In closure piece 3 represented in FIGS. 4A-4C, a nonreturn valve is provided to prevent a backflow. As FIGS. 4a and 4b show, a ball valve seat 21 is made at the outlet end of filling opening 17. Several ball valve cage hooks 23 are placed around this ball valve seat 21. Together with ball valve seat 21 these cage hooks 23 enclose a cage. Valve face 22 represented in FIG. 4C is placed, free-floating, in this cage.

As FIG. 5 shows, opening 8 on tip 9 of hollow pins 6 is made as a slit 11 shaped like a cross. As can also be seen in FIG. 5, tips 10 of solid pins 5 are rounded. It can further be seen in FIG. 5 that both the solid and hollow pins have a cone shape. In the same radial planes, the diameters of hollow pins 6 are larger than those of solid pins 5.

FIG. 5 shows the design of a knurl 20 on the periphery of cylinder 1.

When using plastic bottles that contain a medicine or a pharmaceutical and that exhibit a pump or dispenser mechanism, closure piece 3 in the seat can receive the dispensing end of this plastic bottle. For use it is necessary to screw cylinder 1 onto closure piece 3.

Figure 6:
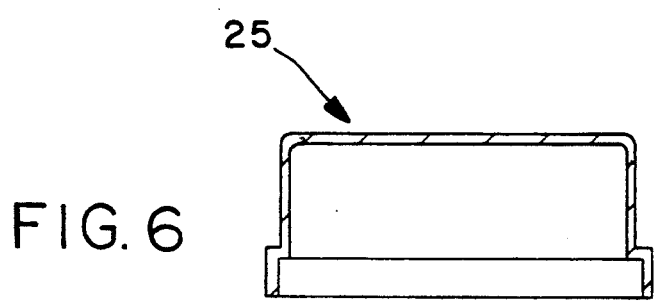

FIG. 6 shows the sectional view of a closure cap 25 that can be placed on cylinder 1 represented in FIG. 1 to protect in particular the tips of solid and hollow pins 5 and 6.

I claim:

1. An applicator, especially useful for treating the scalp, the applicator comprising:
   a cylindrical member having a top wall with a front face and a rear face, the front face having an array of first and second projections extending therefrom, the first projections being solid in cross section and the second projections being tubular and opening through the rear face;
   the first and second projections being arranged in concentric circles with at least some of the first projections being arrayed in a first circle having the largest diameter and the second projections being arrayed in at least one circle of the diameter less than the first circle with others of the first projections being arrayed in a third circle of a diameter less than the second circle; an additional array of second projections disposed within the third circle, the height of the projections being so configured that the closer the projections are to the center of the array of projections, the less their height whereby the projections have ends defining a concave distribution of surfaces;
   a closure member positioned adjacent the rear face of the top wall of the cylindrical member in spaced relation thereto to define a space between the rear face and closure member;
   an opening through the closure member in communication with the space; and
   a one way valve disposed in the opening for allowing liquid to flow through the opening into the space while inhibiting flow of liquid from the space back out of the opening, whereby measured amounts of liquid determined by the volume of the space are dispensed through the second projections.

2. The applicator of claim 1, wherein the closure member has a neck portion of a diameter less than that of the cylindrical member for coupling the applicator to a container having a mouth of a diameter less than the closure member.

3. The apparatus of claim 2, wherein the volume of the space is in the range of 0.1-5 ml.

4. The applicator of claim 3, wherein the volume of the space is in the range of 0.25-2.5 ml.

5. The applicator of claim 1, wherein the closure member and cylindrical member are joined by a threaded connection.

6. The applicator of claim 1, wherein a second projection is disposed at the center of the concentric circles.

7. The applicator of claim 1, wherein a circular cap is detachably fitted to the cylindrical member over the projections.

* * * * *